United States Patent
Dully

(10) Patent No.: US 7,800,914 B2
(45) Date of Patent: Sep. 21, 2010

(54) APPARATUS AND METHOD FOR STORING AND REGULATING ACCESS TO PORTABLE ELECTRONIC DEVICES

(76) Inventor: David Dully, 131 S. 17th St., Fernandina, FL (US) 32034

(*) Notice: Subject to any disclaimer, the term of this patent is extended or adjusted under 35 U.S.C. 154(b) by 394 days.

(21) Appl. No.: 11/758,205

(22) Filed: Jun. 5, 2007

(65) Prior Publication Data
US 2008/0106870 A1 May 8, 2008

Related U.S. Application Data

(60) Provisional application No. 60/804,236, filed on Jun. 8, 2006.

(51) Int. Cl.
*H05K 5/00* (2006.01)
(52) U.S. Cl. ........................... 361/756; 361/800
(58) Field of Classification Search ............ 361/750, 361/756, 790, 797, 800, 727, 741, 686, 802; 439/377
See application file for complete search history.

(56) References Cited

U.S. PATENT DOCUMENTS

| | | | |
|---|---|---|---|
| 5,564,803 A | 10/1996 | McDonald et al. | |
| 5,702,115 A | 12/1997 | Pool | |
| RE35,743 E | 3/1998 | Pearson | |
| 6,022,088 A | 2/2000 | Metzler | |
| 6,218,796 B1* | 4/2001 | Kozlowski | 318/280 |
| 6,246,905 B1 | 6/2001 | Mogul | |
| 6,339,732 B1 | 1/2002 | Phoon et al. | |
| 6,435,109 B1 | 8/2002 | Dell et al. | |
| 6,462,944 B1* | 10/2002 | Lin | 361/679.5 |
| 6,545,863 B2 | 4/2003 | Huggins | |
| 6,626,445 B2 | 9/2003 | Murphy et al. | |
| 6,655,545 B1 | 12/2003 | Sonneborn | |
| 6,769,568 B2 | 8/2004 | Bonini et al. | |
| 6,775,591 B1 | 8/2004 | Shoenfeld | |
| 7,055,833 B2* | 6/2006 | Wixted et al. | 280/47.34 |
| 7,130,190 B1* | 10/2006 | Baker | 361/695 |
| 2002/0165641 A1 | 11/2002 | Manalang et al. | |
| 2003/0182019 A1 | 9/2003 | Bonini et al. | |
| 2003/0201697 A1 | 10/2003 | Richardson | |
| 2004/0036386 A1 | 2/2004 | Olivera | |
| 2004/0236175 A1 | 11/2004 | Boone et al. | |
| 2004/0262867 A1 | 12/2004 | Arceta et al. | |
| 2005/0113969 A1 | 5/2005 | Spano, Jr. et al. | |

* cited by examiner

*Primary Examiner*—Hung S Bui
(74) *Attorney, Agent, or Firm*—Shook, Hardy & Bacon L.L.P.

(57) ABSTRACT

A storage unit and associated methods of use enable clinicians to store portable electronic devices in a centralized location while ensuring that proper authorization is needed to access the devices. The storage unit is formed with an enclosure for housing portable electronic devices. A plurality of shelves are disposed within the enclosure, each being sized for supporting a portable electronic device. One or more access doors are mounted onto the enclosure and moved between a closed position preventing access to housed electronic devices and an open position where the electronic devices may be viewed and accessed. Each access door has a locking mechanism coupled therewith to selectively maintain the access door in the closed position. Optionally, the locking mechanism receives input regarding a request for access to the enclosure and automatically unlocks the associated access door when the input received is associated with an authorized request for access.

14 Claims, 5 Drawing Sheets

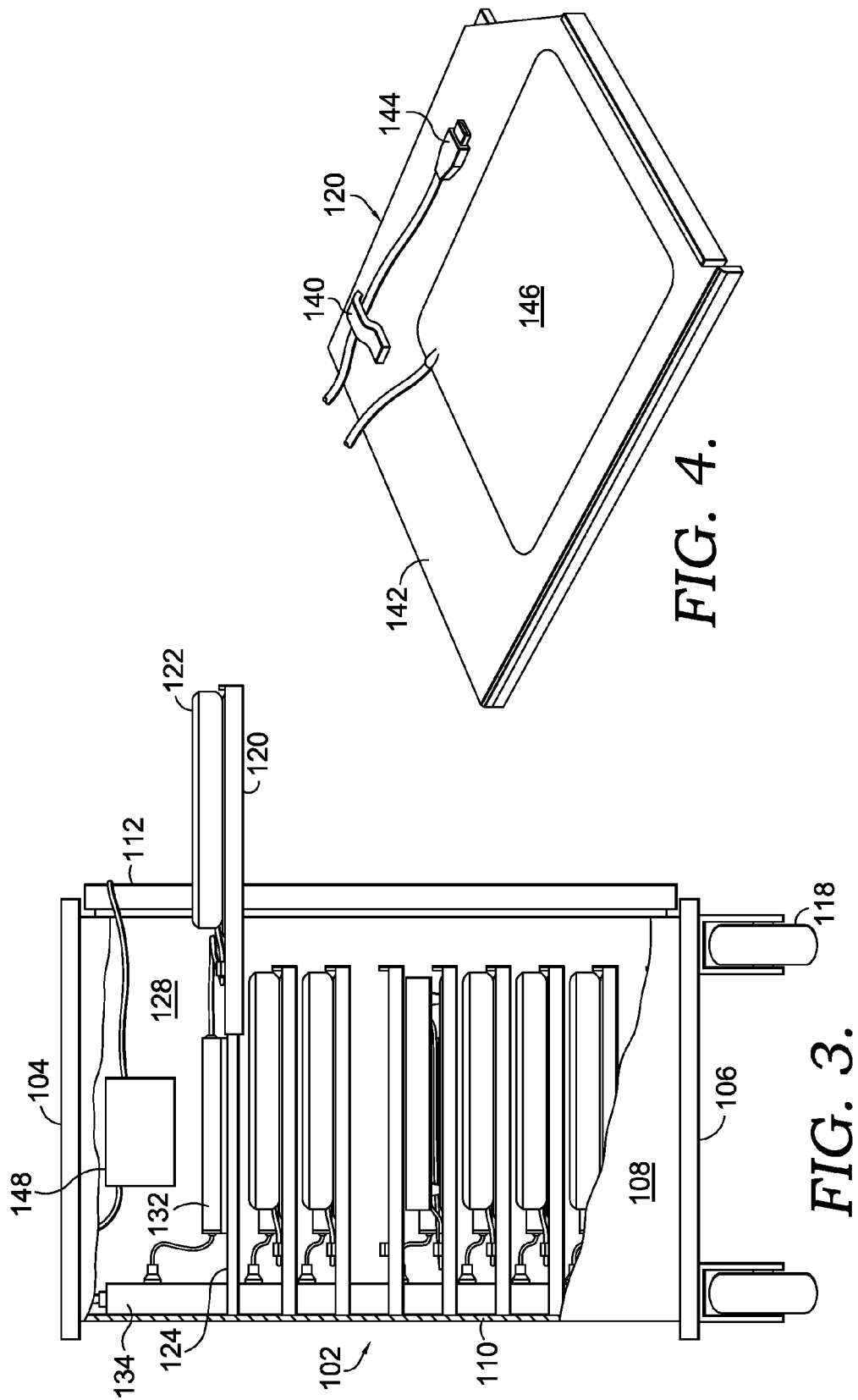

APPARATUS AND METHOD FOR STORING AND REGULATING ACCESS TO PORTABLE ELECTRONIC DEVICES

CROSS-REFERENCE TO RELATED APPLICATIONS

This application claims priority to commonly owned U.S. provisional application Ser. No. 60/804,236 filed Jun. 8, 2006, incorporated by reference in its entirety.

STATEMENT REGARDING FEDERALLY SPONSORED RESEARCH OR DEVELOPMENT

Not applicable.

BACKGROUND OF THE INVENTION

Portable electronic devices, such as laptop computers, PDAs, and the like, are used in modern clinical settings in the delivery of patient care. These devices allow clinicians to perform a variety of care-related tasks, examples of which include viewing a patient's electronic medical record (EMR) or collaborating with other clinicians about a particular patient's plan of care, all without having to be at a fixed location. By providing clinicians with tools that enable faster access to the information they need to make informed care delivery decisions, treatment outcomes and patient satisfaction may be improved.

Clinical organizations often have a number of portable electronic devices that are shared amongst numerous individuals performing clinical tasks. For example, a team of anesthesiologists in a hospital may share use of the same set of laptop computers or PDAs that are loaded with software relevant to the tasks that they commonly perform. These devices, however, are often the subject of theft due to their high value and portability. Not only is it expensive to replace these devices, but sensitive patient information may also be stored on them. Additionally, these items are easy to misplace in clinical settings where many other electronic devices are present. Each clinician that shares use of a device may also choose to store the device at a secure location that they will remember, but other clinicians may not be familiar with, causing confusion and wasted time searching for the device. Portable electronic devices also typically have a power supply, also called a "power converter", for drawing A/C power during normal operation or recharging batteries within the device. In a clinical setting, these power supplies are also easy to misplace and difficult to distinguish from one another when many devices are present. Clinicians, therefore, have found elusive a solution for the organized storage and recharging of portable electronic devices.

SUMMARY OF THE INVENTION

A storage unit provides for the organized and secure retention of portable electronic devices. The storage unit is configured to allow access to the electronic devices within the unit only by authorized clinicians. By aggregating a number of electronic devices together in a centralized location, clinicians can more easily locate a needed device that is shared with other individuals.

In one aspect, the storage unit is formed with an enclosure for housing portable electronic devices and associated power supplies. A plurality of shelves are disposed within the enclosure, each being sized for supporting a portable electronic device. One or more access doors are mounted onto the enclosure and moved between a closed position preventing access to housed electronic devices and an open position where the electronic devices may be viewed and accessed. Each access door has a locking mechanism coupled therewith to selectively maintain the access door in the closed position. A chamber is also formed within the enclosure where power supplies associated with the portable electronic devices may be stored.

The storage unit may optionally have casters so that the unit may be easily moved to another location within a clinical environment, such as a hospital. Additionally, the locking mechanism may receive input regarding a request for access to the enclosure and automatically unlock each access door when the input received is associated with an authorized request for access to the storage unit. Sensors may also be provided on the plurality of shelves to detect where electronic devices are currently present, as well as when devices are removed and return to specific shelves.

In another aspect, the storage unit is formed as an enclosure that houses portable electronic devices that are supported by a plurality of shelves disposed within the enclosure. One or more access doors are mounted onto the enclosure and moved between a closed position preventing access to housed electronic devices and an open position where the electronic devices may be viewed and accessed. A locking mechanism is coupled with and selectively maintains each access door in the closed position. Each locking mechanism receives input regarding a request for access to the enclosure and automatically unlocks the associated access door when the input received is associated with an authorized request for access to the storage unit.

A method for regulating access to an enclosure is provided in another aspect. The enclosure contains a plurality of shelves that are each sized for supporting a portable electronic device, and access to the enclosure is gained through one or more access doors mounted on the enclosure. According to the method, input is received regarding a request for access to the enclosure while the one or more access doors are secured in a closed position. The input is processed to determine if an authorized request for access to the enclosure has been made. If so, then a locking mechanism that secures the one or more access doors in the closed position moves to an unlocked position to allow the doors to be moved from the closed position to the open position, allowing access and removal from the enclosure of portable electronic devices positioned on the plurality of shelves.

Additional advantages and features of the invention will be set forth in part in a description which follows, and in part will become apparent to those skilled in the art upon examination of the following, or may be learned by practice of the invention.

BRIEF DESCRIPTION OF THE SEVERAL VIEWS OF THE DRAWINGS

In the accompanying drawings, which form a part of the specification and are to be read in conjunction therewith and in which like reference numerals are employed to indicate like parts in the various views:

FIG. 3 is a side elevational view of the storage unit of FIG. 1 with the side wall partially removed and one divider wall removed to show an extended shelf supporting a portable electronic device with an associated power supply;

FIG. 4 is a perspective view of one shelf having a resilient clip and a pressure sensor;

DETAILED DESCRIPTION OF THE INVENTION

Figure 1:
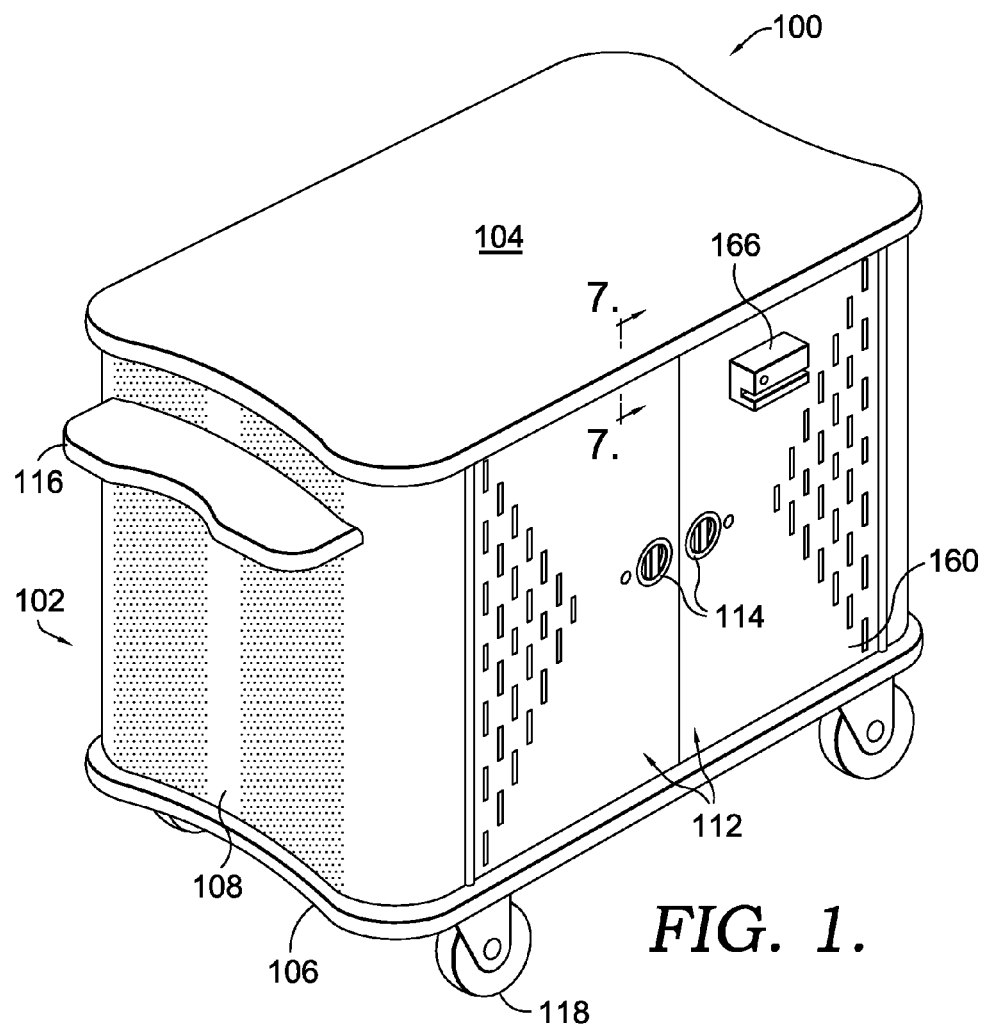
FIG. 1 is a perspective view of an embodiment of a storage unit holding portable electronic devices and with access doors in the closed position.
Figure 2:
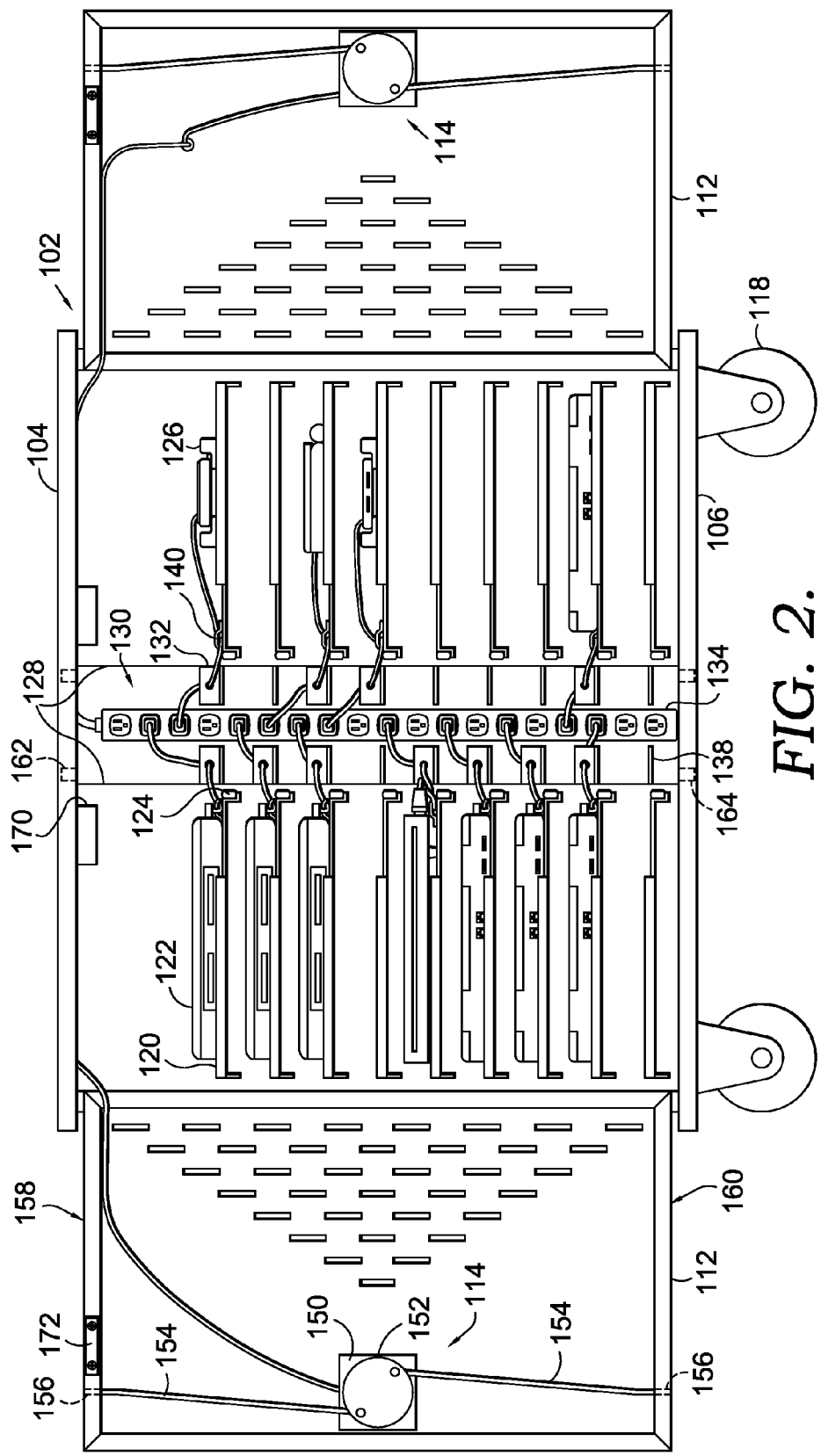
FIG. 2 is a front elevational view of the storage unit of FIG. 1 with the access doors in the open position.

One embodiment of a storage unit 100 having regulated access to contents housed within the unit, such as portable electronic devices, is shown generally in FIGS. 1 and 2. The storage unit 100 is particularly well suited for use in clinical settings where a group of authorized clinicians may share use of various portable electronic devices. As one example, the portable electronic devices may include laptop computers, PDAs, tablet PC's, cellular phones, and the like, which may display various types of clinical information (e.g., electronic medical records (EMR) or other documentation, diagnostic images, etc.) and facilitate communication with other portable electronic devices, computing devices or networks. The storage unit 100 provides a centralized location where a number of shared devices may be stored while ensuring that only authorized clinicians may access the devices. Additionally, the storage unit 100 is configured to provide an organized layout where specific devices can be easily located and differentiated from other devices within the unit 100.

The storage unit 100 is formed generally by an enclosure 102 with a ceiling 104, a floor 106, a pair of sidewalls 108, a back wall 110 and a pair of front access doors 112. Locking mechanisms 114 regulate the opening of the access doors 112 for obtaining access to the enclosure 102. An exterior shelf 116 extends from each sidewall 108, and set of casters 118 are mounted onto the floor 106 of the enclosure 102 for portability of the storage unit 100 in a clinical environment (e.g., hospital, physician's office, etc.). It should be understood that the overall shape of the enclosure 102 shown in FIGS. 1 and 2 is exemplary. Additionally, the enclosure 102 may one, two, or any number of access doors 112 mounted onto the enclosure 102 as a matter of design choice.

In the embodiment illustrated in FIG. 2, the pair of access doors 112 are pivoted to a fully opened position to reveal a plurality of shelves 120 onto which may be placed portable electronic devices 122 of a particular size. The shelves 120 are preferably mounted upon drawer slides 124 (e.g., roller or ball bearing) as seen in further detail in FIG. 3. The drawer slides 124 are fixedly positioned within the enclosure 102 to allow for extension of the shelves 120 laterally outward. This facilitates removal of electronic devices 122 from specific shelves 120 without disturbing electronic devices 122 on other shelves 120. The shelves 120 may have uniform vertical spacing between one another of a limited dimension in order to limit the sizes of specific portable electronic device 122 that may be stored on certain shelves 120 within the storage unit 100. For instance, the shelf spacing may limit the storage of items larger than a full-size laptop computer on most shelves 120. Furthermore, specifically dimensioned bays 126 may be formed on particular shelves 120 to provide a storage region for small electronic devices 122 (e.g., PDAs) while preventing larger electronic devices 122 from being placed on such shelves 120. Those of skill in the art will appreciate, however, that other shelf sizes and configurations may be selected based on the types of portable electronic device 122 desired to be stored within the unit 100.

A pair of divider walls 128 extend vertically through the enclosure 102 between first and second columns of shelves 120. The divider walls 128 define a central chamber 130 therebetween into which a power supply 132 (i.e., a AC-to-DC power converter) for each of the portable electronic devices 122 may be stored. A multi-outlet power strip 134 is mounted onto the back wall 110 of the enclosure 102 and may be plugged into a standard wall A/C outlet of a building. Each power supply 132 plugs into the power strip 134 to provide power (converted to D/C) to a specific electronic device 122. The divider walls 128 also have cutouts (not shown) to allow power supply cords 136 to extend therethrough to reach the electronic devices 122 stored on the shelves 120. A plurality of horizontally flanges 138 extend from the divider walls 128 within the central chamber 130 and are each generally positioned adjacent to one of the shelves 120 to support a power supply 132 that is associated with one particular electronic device 122 that is to be placed on the adjacent shelf 120. For instance, each shelf could be designated with a particular position (e.g., Column 1, Shelf 5) and a particular electronic device 122 associated with that position by placing a label on the exterior of the electronic device 122 denoting the assigned position for the device 122. This ensures that when the electronic device 122 is placed on a shelf, the power supply 132 associated with that particular electronic device 122 is conveniently located in an adjacent position and may be easily plugged in to recharge the battery within the electronic device 122.

As seen in further detail in FIG. 4, a resilient clip 140 is attached to the upper surface 142 of each shelf 120 and serves to retain an end connector 144 of the power supply cord 136 on the shelf 120 through extension and retraction of the shelves 120. This allows a clinician to easily plug the end connector 144 into a electronic device 122 without having to search for the end connector 144 within the enclosure 102. Adjacent to the clip 140 on each shelf 120 is a pressure sensor 146, which may be in the form of a thin membrane. Exemplary pressure sensors 146 that are suitable include piezoelectric pressure sensors or pressure transducers. The pressure sensor 146 detects the presence of an electronic device 122 on the shelf 120 by the weight of the electronic device 122 pressing on the pressure sensor 146. When a pressure change is detected, either by a electronic device 122 being placed on or removed from the pressure sensor 146 surface, a signal is transmitted to circuitry 500 disposed within a housing 148 mounted to the enclosure 102, and seen in further detail in FIG. 5. Circuitry 500 processes the signal received from the pressure sensor 146 to determine if an increase or decrease of pressure has occurred from the last signal received from the particular pressure sensor 146 transmitting the signal. Additionally, circuitry 500 registers the time at which the signal is received from the particular pressure sensor 146, which allows for logging of the amount of time a particular electronic device 122 has been "checked out" of the storage unit 100. As an alternative to the pressure sensor, an optical sensor (e.g., an infrared sensor) or other type of sensor may be provided for sensing the presence of an electronic device 122 upon a particular shelf 120. The functionality of circuitry 500 will be explained in further detail herein.

Figure 5:
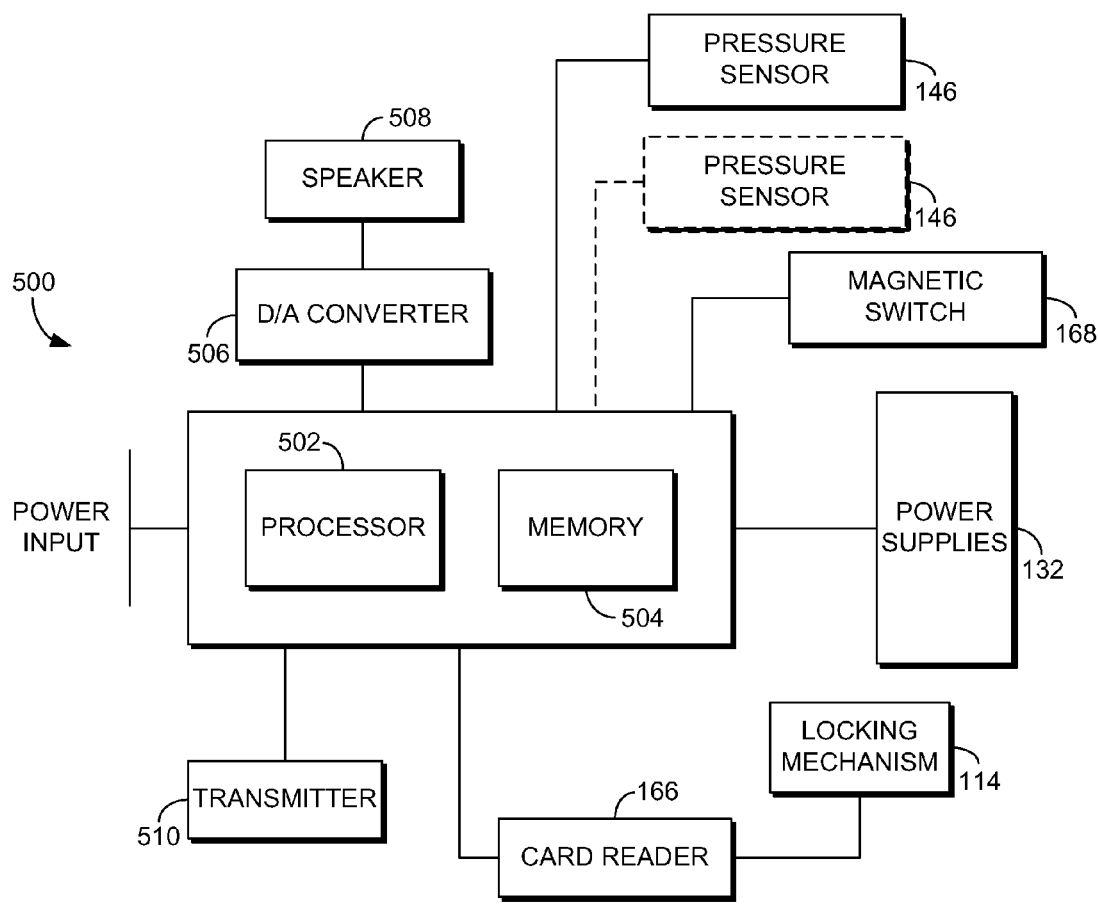
FIG. 5 is a schematic block diagram of an embodiment of circuital architecture of the storage unit.

Returning to FIGS. 1 and 2, and with reference to FIG. 5, one locking mechanism 114 is mounted onto each of the access doors 112. Each locking mechanism 114 has an actuator 150, for example, a solenoid, operating on electrical current regulated by the circuitry 500. The actuator 150 turns a hub 152 having a pair of opposed locking rods 154 pivotably mounted thereto. When one of the access doors 112 is in the closed position shown in FIG. 1, the rotation of the hub 152 extends the locking rods 154 through apertures 156 in top and bottom sections 158 and 160 of each access door 112 and into the slots 162 and 164 in the ceiling 104 and floor 106, respectively, of the enclosure 102 to lock the door 112 in place.

Clinicians may be provided by a clinical organization with an access card (not shown) having a readable magnetic strip that stores information regarding authorization for access to the electronic devices 122 within the storage unit 100. Such an access card would thus function in a similar way to known cards having a readable magnetic strip, such as a consumer credit or debit card. Accordingly, the storage unit 100 has an electronic card reader 166 mounted on the external surface 160 of one of the doors 112. The electronic card reader 166 scans the magnetic strip present on an access card to verify whether the clinician associated with the card is authorized to access the devices 122 within the storage unit 100. Upon scanning, the card reader 166 sends a signal to the circuitry 500 to verify whether the access card should grant storage unit access. If so, then the circuitry 500 allows a flow of electrical current to energize the actuator 150 and cause hub 152 rotation and retraction of the locking rods 154 from the slots 162 and 164, thereby allowing the doors 112 to be fully opened to the position depicted in FIG. 2. In an alternative embodiment, the card reader 166 may be replaced with a touch keypad (not shown) or other device allowing a clinician to enter certain information (e.g., a confidential alphanumerical passcode) confirming authorization to access electronic devices 122 within the storage unit 100.

It should be understood that other types of locking mechanisms 114 may be implemented with the storage unit 100. For example, mechanisms may be mounted directly onto the enclosure 102 instead of on the access doors 112. Such a locking mechanism may extend locking rods 154 or the like through either or both of the apertures 156 in the top and bottom sections 158 and 160 of each access door 112 to maintain the doors 112 in the closed position.

Figure 7:
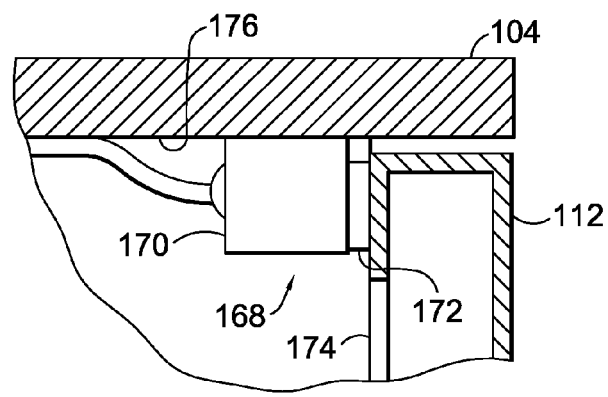
FIG. 7 is a fragmentary view, partially in section, showing the contact switch mounted with the enclosure and one access door to indicate when the access door in the closed position.

With reference to FIGS. 2 and 7, an magnetic contact switch 168 may be provided, in one embodiment, with each access door 112. Each contact switch 168 includes a wired magnetic component 170 mounted to the underside 176 of the ceiling 104 of the enclosure 102 and an unwired magnetic component 172 mounted onto an inside surface 174 of one of the access doors 112. When one access door 112 is moved to the closed position, the wired magnetic component 170 and unwired magnetic component 172 are in close proximity to one another to form a completed circuit, as seen in FIG. 7. Circuitry 500 detects the completed circuit and controls the electrical current flow to the actuator 150 of the associated access door 112 to enable locking of the door 112. Thus, when one of the access doors 112 is moved to the closed position, it is automatically locked without requiring further action from the clinician accessing the storage unit 100.

In accordance with one embodiment, the circuitry 500 includes a processing unit 502, such as a microprocessor, microcontroller or application-specific integrated circuit, along with associated memory 504. By way of example, the processing unit 502 handles control signals and/or data signals of various types. For instance, one or more pressure sensors 146 generate a signal that is transmitted to the processing unit 502. The memory 504 stores embedded software that is used by the processing unit 502 to determine pressure values based on the signal received from a specific pressure sensor 146 and also causes the processing unit 502 to note the time when the signal was received and the specific sensor 146 from which the signal originated. The embedded software is also used in the verification of authorization information (e.g., retrieved from the scanned access card) for accessing the storage unit 100. Circuitry 500 optionally includes a digital-to-analog (D/A) converter 506 connected with a speaker 508. When the locking mechanisms 114 move to the unlocked position, so that either or both of the access doors 112 may be opened, the circuitry 500 notes the time. If the circuitry 500 does not detect a completed circuit or "closed access door" condition from each of the magnetic contact switches 168 within predetermined period of time (e.g., 60 seconds), the circuitry 500 generates an alarm signal that is transmitted to the D/A converter 506, which forces the speaker 508 to produce an audible alarm to remind the clinician to close all of the access doors 112 to the storage unit 100. Circuitry 500 may also include a transmitter 510 for communication with a clinical network via a remote receiver (not shown), so that information logged and stored by the circuitry 500 regarding storage unit 100 access, an alarm situation, or electronic device 122 inventory, return to and/or retrieval from the unit 100 may be monitored by a clinical organization. Furthermore, the exemplary architecture of the circuitry 500 ensures that if the main power input to the storage unit 100 is not provided, then access to the enclosure 102 is forbidden. More specifically, if the storage unit 100 is simply unplugged, the electronic card reader 166 will not be able to scan access cards, and no electrical current will flow to the actuators 150, both steps being necessary to unlock the access doors 112.

Figure 6:
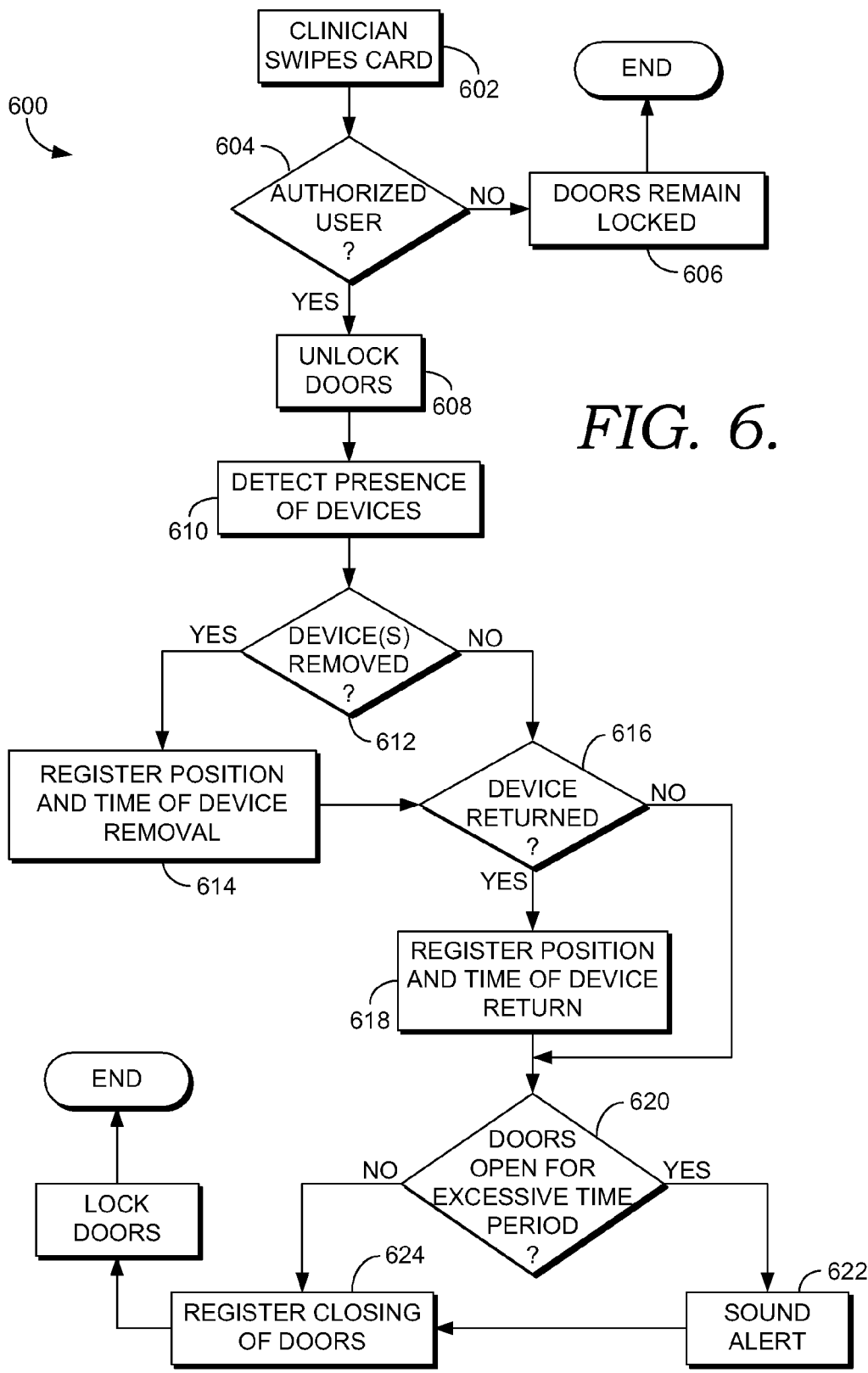
FIG. 6 is a flow chart illustrating one process for regulating access to the portable electronic devices within the storage unit.

One exemplary process 600 for regulating access to the electronic devices 122 within the storage unit 100 is illustrated in FIG. 6. A clinician will swipe an assigned access card through the electronic card reader 166, in step 602. Based on information detected on the card, a decision is made in step 604 regarding whether an authorized request for access has been made. If the request for access is not authorized, then the access doors 112 of the storage unit 100 remained locked in step 606 and thereafter the process 600 ends. Otherwise, in step 608, an authorized request for access causes the locking mechanisms 114 to unlock each of the access doors 112. Each pressure sensors 146 then detects the presence of electronic devices 122 and transmits representative signals to the circuitry 500, in step 610, allowing the circuitry 500 to register the positions (i.e., particular column and shelves 120) where electronic devices 112 are presently located while also logging the time of the access doors 112 unlocking. Thereafter, the pressure sensors 146 detect the removal from and return of electronic devices 122 to the shelves 120 while one or more of the access doors 112 are opened, as will be explained herein.

In step 612, a determination is made as to whether electronic device 122 removal is detected by any particular pressure sensors 146. If none of the pressure sensors detect the removal of electronic devices 122, the process continues at step 616. Otherwise, if electronic device removal is detected, then in step 614, the circuitry 500 registers the position and time of removal for each electronic device 122 removed. Then, in step 616, a determination is made as to whether electronic device 122 return is detected by any particular pressure sensors 146. If none of the pressure sensors detect the return of electronic devices 122, the process continues at step 620. Otherwise, if electronic device return is detected, then in step 618, the circuitry 500 registers the position and time of return for each electronic device 122 returned.

During the process 600, the circuitry 500 is detecting for a closed circuit condition with each magnetic contact switch 168, which signals that the access doors 112 are closed and the contents of the enclosure 102 are secure. Based on the time noted for when the locking mechanisms 114 unlock the access doors 112 (in step 608), the circuitry 500 determines, in step 620, whether a excessive period of time has elapsed since the access doors 112 were unlocked based on a predetermined time limit. If the predetermined time limit is exceeded before the circuitry detects the closed circuit condition for the magnetic contact switches 168, an alarm signal is generated by the circuitry 500 and an audible alert provided by the speaker 508 in step 622. Otherwise, detection of the closed circuit condition for each of the magnetic contact switches 168 before the predetermined time limit is exceeded causes the process to move directly to step 624. Returning to step 622, the audible alarm will cease once the closed circuit condition for each of the magnetic contact switches 168 is detected. At the point where the circuitry 500 detects the closed circuit condition for each switch 168, then in step 624, the closing of the doors is registered. Circuitry 500 then controls the electrical current flow to the actuator 150 of each locking mechanism 114 to enable locking of the access doors 112, in step 626. Thereafter, the process 600 ends.

As can be seen, the storage unit 100 and associated methods of operation thereof provide for controlled and shared access to portable electronic devices in a clinical environment. Since certain changes may be made in the above invention without departing from the scope hereof, it is intended that all matter contained in the above description or shown in the accompanying drawing be interpreted as illustrative and not in a limiting sense. It is also to be understood that the following claims are to cover certain generic and specific features described herein.

What is claimed is:

1. An apparatus for storing and regulating access to portable electronic devices having associated power supplies, comprising:
    an enclosure;
    a plurality of shelves disposed within the enclosure, each shelf of the plurality of shelves being sized for supporting a portable electronic device;
    at least one access door mounted on the enclosure and movable between an open position and a closed position relative to the enclosure;
    a locking mechanism coupled with the at least one access door to selectively maintain the at least one access door in the closed position, wherein the locking mechanism is adapted to receive input regarding a request for access to the enclosure and automatically unlock the at least one access door to allow movement of the at least one access door from the closed position to the open position when the input received is associated with an authorized request for access to the enclosure; and
    a chamber formed within the enclosure for at least partially storing the power supplies associated with the portable electronic devices.

2. The apparatus of claim 1, wherein the locking mechanism includes a card reader for scanning information encoded on an access card and a power lock operable in response to the scanned information.

3. The apparatus of claim 2, further comprising circuitry coupled with the locking mechanism to process the information scanned from the access card by the card reader to determine if an authorized request for access to the enclosure has been made, and if so, generate a control signal directing the power lock to move to the unlocked position.

4. The apparatus of claim 1, further comprising at least one bay formed on the plurality of shelves, each bay defining a specific space into which one of the portable electronic devices may be inserted.

5. The apparatus of claim 1, further comprising:
    a plurality of first sensors mounted onto the plurality of shelves for detecting the presence of portable electronic devices on the shelves; and
    circuitry coupled with the plurality of sensors to register the location of particular shelves of the plurality of shelves where portable electronic are disposed.

6. The apparatus of claim 1, further comprising:
    at least one second sensor detecting whether the at least one access door is in the closed position relative to the enclosure; and
    circuitry coupled with the at least one second sensor to register a first time when the at least one second sensor does not detect one door of the at least one access door in the closed position and generating an alarm signal if the at least one second sensor does not detect the one door of the at least one access door in the closed position within a predetermined amount of time from the first time.

7. The apparatus of claim 1, further comprising a power strip disposed within the chamber and adapted for electrical coupling with the power supplies associated with the portable electronic devices, the power strip being capable of electrical coupling with a standard A/C power outlet.

8. An apparatus for storing and regulating access to portable electronic devices, comprising:
    an enclosure;
    a plurality of shelves disposed within the enclosure, each shelf of the plurality of shelves being sized for supporting a portable electronic device;
    at least one access door mounted on the enclosure and movable between an open position and a closed position relative to the enclosure;
    a locking mechanism coupled with the at least one access door to selectively maintain the at least one access door in the closed position, the locking mechanism being adapted to receive input regarding a request for access to the enclosure and automatically unlock the at least one access door to allow movement of the at least one access door from the closed position to the open position when the input received is associated with an authorized request for access to the enclosure; and
    circuitry coupled with the locking mechanism to process the input received by the locking mechanism to determine if an authorized request for access to the enclosure has been made, and if so, generate a control signal directing the locking mechanism to unlock the at least one access door.

9. The apparatus of claim 8, wherein the locking mechanism includes a card reader for scanning information encoded on an access card and a power lock operable in response to the scanned information.

10. The apparatus of claim 8, further comprising at least one bay formed on the plurality of shelves, each bay defining a specific space into which one of the portable electronic devices may be inserted.

11. The apparatus of claim 8, further comprising a plurality of first sensors mounted onto the plurality of shelves for detecting the presence of portable electronic devices on the shelves, wherein the circuitry is coupled with the first plurality of sensors to register the location of particular shelves of the plurality of shelves where portable electronic are disposed.

12. The apparatus of claim 8, further comprising at least one second sensor detecting whether the at least one access door is in the closed position relative to the enclosure, wherein the circuitry is coupled with the at least one second sensor to register a first time when the at least one second sensor does not detect one door of the at least one access door in the closed position and generate an alarm signal if the at least one second sensor does not detect the one door of the at least one access door in the closed position within a predetermined amount of time from the first time.

13. The apparatus of claim 8, further comprising a chamber formed within the enclosure, wherein the portable electronic devices have associated power supplies capable of being at least partially stored within the chamber.

14. The apparatus of claim 13, further comprising a power strip disposed within the chamber and adapted for electrical coupling with the power supplies associated with the portable electronic devices, the power strip being capable of electrical coupling with a standard A/C power outlet.

* * * * *